United States Patent [19]

Billings

[11] Patent Number: 5,063,049

[45] Date of Patent: Nov. 5, 1991

[54] DISINFECTANT NAIL POLISH REMOVER

[76] Inventor: Calvert Billings, 23221 Peralta, Ste. H, Laguna Hills, Calif. 92653

[21] Appl. No.: 535,512

[22] Filed: Jun. 11, 1990

[51] Int. Cl.$^5$ ............................................... A61K 7/04
[52] U.S. Cl. ..................................... 424/61; 424/401; 422/28
[58] Field of Search .................................. 424/61, 401

[56] References Cited

U.S. PATENT DOCUMENTS 4,762,703  8/1988  Abrutyn ................................. 424/61

OTHER PUBLICATIONS

Roda, K. P., Studies on 2-pyrazolines, 1989, pp. 51–52.
Mehta, K. J., Studies on Chalcones, I Preparation of Substituted benzal-y-acetothymols, 1978, pp. 241–242.
Foltinova, P., Synthesis and Biological Activity of 6-(y-hydroisopropyl-2-methyl phenyl/AZO)-2-R--thiobenzothiazoles, pp. 1–15 (Eng.).
Arakawa, Masazumi, Antibacterial Agents for Industrial Use, Parachlormetaxylenol, 1979, pp. T473–T478 (Japan).

*Primary Examiner*—Thurman K. Page
*Assistant Examiner*—William E. Benston, Jr.
*Attorney, Agent, or Firm*—Francis X. LoJacono

[57] ABSTRACT

A nail polish remover combined with a disinfectant solution comprising a fungicidal agent and a bactericidal agent that includes a solvent and a carrier which allows the disinfectant solution to penetrate the nail plate so as to reach the fungus and/or bacteria infected areas around and under the nail plate.

5 Claims, No Drawings

DISINFECTANT NAIL POLISH REMOVER

FIELD OF THE INVENTION

The present invention relates generally to a combination fungicidal and bactericidal composition and more particularly to a composition defining a fungicidal and/or bactericidal nail polish remover that provides a positive antiseptic wash wherein the liquid nail polish remover consists of the ingredients of a fungicide and a bactericide together with a carrier solution whereby the fungicide and bactericide can be combined with an acetone or non-acetone solution so as to allow the fungicide and bactericide to penetrate the pores of the nail plate while removing the nail polish from the nail.

BACKGROUND OF THE INVENTION

As is well know in the art, various problems and difficulties are encountered in providing suitable means for controlling, preventing and eradicating fungi and bacterial growth that is prevalent with the use of nail polish and more particularly with the use of artificial nails that are glued or otherwise secured to the natural nails. Due to the widespread use of artificial nails, the problem of fungi, mold and bacteria has become universally recognized by manicurists who must spend considerable time treating infected nails after the nail polish is removed. This time-consuming operation which is required to deal with these problems has become an added expense and an obstacle for manicurists.

Certain fungi live on keratin, the protein that forms the nail plate. When a fungus begins to grow, it can actually lift the nail plate up and off the nail bed. This can ultimately result in the loss of the whole nail.

Thus, it is an important object of the present invention to provide a nail polish remover that removes the polish from a nail and at the same time acts as a disinfectant to kill the growth fungus, mold or bacteria around and under the nail.

Another object of the present invention is to provide a nail polish remover of this character wherein the fungicidal and bactericidal ingredients are compatible with an acetone or a non-acetone base.

Still another object of the invention is to provide a nail polish remover that further includes ingredients that carry the fungicide and bactericide through the pores of the nail plate or through both an artificial nail and the natural nail to which it is attached.

A further object of the invention is to provide a disifectant for use with a nail polish remover that consists of a mixture of butyl acetate, ethyl acetate, isopropyl alcohol, thymol crystals, and parachlormetaxylenol, wherein the acetates and alcohol together act as a carrier and solvent.

Accordingly, a substantial need exists in the art for a composition that can be used both as a nail polish remover and disinifectant for killing a fungus, mold and bacteria growth around and under the nail plate of a finger at the same time the polish is removed.

DISCLOSURE OF THE INVENTION

The present invention defines a process for forming a fungicidal and bactericidal composition in combination with a nail polish remover solution. However, the preferred form of the invention is to add the fungicidal and bactericidal composition to either an acetone based or a non-acetate based nail polish remover. Thus, with the use of the present invention, not only is the nail polish removed from the finger nail or toe nail, but the compound will at the same time eradicate fungus, mold and bacteria growth under and around the nail plate. There are certain types of fungi that live on keratin, which is the protein that forms the nail plate. If a fungus is allowed to continue growing for a time without proper treatment, the nail becomes infected and the nail plate will lift off the nail bed. This often results in the loss of the whole nail.

The carrier ingredient of the composition allows the fungicide as well as the bactericide to penetrate the pores of the nail to attack the fungus growth at the same time the polish remover is being applied. Thus, the composition consists generally of a fungicidal substance and a bactericidal substance that is combined with a carrier and/or solvent that includes butyl acetate, ethyl acetate and isopropyl alcohol. The fungicide consist of parachlormetaxylenol, with thymol crystals being used as the bactericidal element of the composition. An optional ingredient of a coloring agent is also employed therewith.

Typically, the basic composition of the present invention contains from about 30 to 50 parts of butyl acetate and from about 30 to 50 parts of ethyl acetate, with about 15 to 25 parts of isopropyl alcohol. These three agents are used both as a solvent and a carrier for the fungicide and bactericide. Accordingly, the parachlormetaxy-lenol contains about 3 to 4 parts thereof and the thymol crystals from about 3 to 4 parts thereof. A 1% coloring solution of between 0.03 to 0.07 may be included therein.

EXAMPLE I

When the ingredients are formulated as a fungicidal nail polish remover, the composition comprises of 38.33 parts of butyl acetate and 36.50 parts of ethyl acetate, with 18.72 parts of isopropyl alcohol. The fungicide is provided by including 3.20 parts of parachlormetaxylenol. The bactericide composition comprises 3.20 parts of thymol crystals. If coloring is used in conjunction with the composition, any suitable coloring may be added thereto such as 0.05 of FD&C blue No. 1 (a 1% solution).

EXAMPLE II

This example repeats the basic agents of Example I. However, the entire composition thereof was mixed with a premixed nail polish remover. The nail polish remover was blended with the composition at an 64 to 1 ratio by volume.

VOLUME III

The agents of Example II are repeated, wherein the nail polish remover comprises a basic acetone composition.

EXAMPLE IV

The agents of Example II are repeated, wherein the nail polish remover comprises a non-acetone composition.

What I claim is:

1. A process for reducing infections located in an area adjacent a nail plate, by reducing fungus, bacteria and mold growth, by applying to the said area a blend of an acetone based nail polish remover to remove nail polish lacquer therefrom in a carrier solution of: parachlormetaxylenol: about 3–4 parts; thymol: about 3–4 parts;

butyl acetate: about 30–50 parts; ethyl acetate: about 30–50 parts; and, isopropyl alcohol: about 15–25 parts.

2. The process of claim 1, in which the said solution contains approximately: 36–39 parts butyl acetate; 35–37 parts ethyl acetate; and, 15–25 parts isopropyl alcohol.

3. The process of claim 1, in which the said solution contains approximately: 0.4 –0.6 parts butyl acetate; 0.4–0.6 parts ethyl acetate; 0.1–0.3 parts isopropyl alcohol; 0.04–0.06 parts thymol; 0.04–0.06 parts parachlorometaxylenol; and, 88–89 parts of said nail polish remover.

4. The process of claim 1, in which the ratio of the said nail polish remover to the carrier solution is 64 to 1 by volume.

5. The process of claim 1, in which the said blend contains up to about 1% coloring solution.

* * * * *